(12) United States Patent
Giezendanner et al.

(10) Patent No.: US 8,226,620 B2
(45) Date of Patent: Jul. 24, 2012

(54) DRAINAGE PUMP UNIT WITH A COUPLING ELEMENT HAVING A CAPACITIVE FILLING LEVEL SENSOR EMBEDDED THEREIN

(75) Inventors: Charles Giezendanner, Morschach (CH); Christoph Gugl, Zurich (CH)

(73) Assignee: Medela Holding AG, Baar (CH)

( * ) Notice: Subject to any disclaimer, the term of this patent is extended or adjusted under 35 U.S.C. 154(b) by 169 days.

(21) Appl. No.: 12/902,263

(22) Filed: Oct. 12, 2010

(65) Prior Publication Data

US 2011/0106028 A1    May 5, 2011

(30) Foreign Application Priority Data

Nov. 5, 2009   (CH) ..................................... 01706/09

(51) Int. Cl.
*A61M 1/00*    (2006.01)
(52) U.S. Cl. ........................................................ 604/319
(58) Field of Classification Search .................. None
See application file for complete search history.

(56) References Cited

U.S. PATENT DOCUMENTS

| | | | |
|---|---|---|---|
| 4,092,860 A | 6/1978 | Arts et al. |
| 4,099,167 A | 7/1978 | Pomerantz et al. |
| 4,898,593 A | 2/1990 | Swisher et al. |

FOREIGN PATENT DOCUMENTS

| | | |
|---|---|---|
| DE | 19645970 | 5/1998 |
| EP | 0853950 | 7/1998 |
| JP | 2161322 | 6/1990 |
| WO | 2007/128156 | 11/2007 |
| WO | 2008/119993 | 10/2008 |
| WO | 2008/141471 | 11/2008 |

OTHER PUBLICATIONS

Swiss Search Report for corresponding Swiss Patent App. No. 01706/2009.

*Primary Examiner* — Jackie Ho
*Assistant Examiner* — Joshua Lee
(74) *Attorney, Agent, or Firm* — McDonnell Boehnen Hulbert & Berghoff LLP

(57) ABSTRACT

A drainage pump unit for aspirating body fluids comprises a suction pump housing and a suction pump arranged in the suction pump housing. A fluid collection container can be secured releasably on the suction pump housing. A flat band-shaped capacitive filling level sensor is arranged on the suction pump housing for the purpose of detecting a filling level in the fluid collection container. The drainage pump unit also comprises an elastically configured coupling element with a first surface and a second surface lying opposite the first surface, and the coupling element, in the secured state of the fluid collection container, bears with the first surface on the filling level sensor and with the second surface on an outer wall of the fluid collection container. By virtue of the elastically configured coupling element, this drainage pump unit permits a filling level measurement even in the case of low filling amounts.

20 Claims, 3 Drawing Sheets

DRAINAGE PUMP UNIT WITH A COUPLING ELEMENT HAVING A CAPACITIVE FILLING LEVEL SENSOR EMBEDDED THEREIN

TECHNICAL FIELD

Drainage pump systems are used to aspirate body liquids and fluids in the medical field. For example, they are used during or after surgical interventions, in wound drainage, in thorax drainage or in liposuction. These drainage pump systems usually have a vacuum pump, one or more fluid collection containers, and a drainage tube connection between patient and fluid collection container. The fluid collection container can be secured releasably on the housing of the drainage pump or is connected to the pump via an external vacuum tube.

With an underpressure being generated in the fluid collection container by means of the suction pump or vacuum pump, the fluid or secretion from a cavity in the patient can be aspirated through the drainage or secretion tube and into the collection container and collected therein. Filters arranged on the pump-side outlet of the collection container protect the suction pump from possible contamination by the aspirated fluid. Drainage pump systems of this kind are disclosed in WO 2007/128156 and WO 2008/141471, for example. The drainage pump systems described there are portable.

Capacitive filling level sensors are suitable for monitoring the drainage profile and the filling level of the fluid collection container. Such filling level sensors are known in the prior art. Thus, JP 2161322 and U.S. Pat. No. 4,099,167 disclose capacitive filling level sensors for determining a filling level of a liquid container, said sensors being mounted on the outside of the liquid container.

U.S. Pat. No. 4,092,860 discloses a capacitive filling level sensor mounted on the outside of a connector piece. This sensor is protected from the outside by a Teflon coating.

DE 196 45 970 discloses a band-shaped capacitive filling level sensor, which is arranged in the interior of a container.

In drainage systems for aspirating body liquids, the filling level sensors are usually located on or in the fluid collection container. WO 2008/119993 thus discloses a fluid collection container with a plurality of filling level sensors mounted on the outside of the container. EP 0 853 950, by contrast, discloses a drainage pump unit with a suction unit and with a fluid collection container, where a capacitive filling level sensor is arranged on the suction unit.

For hygiene reasons, fluid collection containers can only be used for a limited time and should therefore be as inexpensive as possible. If the filling level sensors are mounted on the fluid collection container, however, the costs of the latter increase. By contrast, filling level sensors mounted on the drainage pump unit have less precision than filling level sensors mounted on the container, particularly in the case of low filling quantities.

SUMMARY

It is therefore an object of the invention to make available a drainage pump unit that eliminates the abovementioned disadvantages.

The drainage pump unit according to the invention for aspirating body fluids by means of a suction pump comprises a suction pump housing and a suction pump arranged in the latter. A fluid collection container is able to be secured releasably on the suction pump housing. Moreover, a flat band-shaped capacitive filling level sensor is arranged on the suction pump housing for the purpose of detecting a filling level in the fluid collection container. According to the invention, the drainage pump unit comprises an elastically configured coupling element with a first surface and a second surface lying opposite the first surface, and the coupling element, in the secured state of the fluid collection container, bears with the first surface on the filling level sensor and with the second surface on an outer wall of the fluid collection container.

By virtue of this coupling element, a possible air gap between the fluid collection container and the sensitive face of the filling level sensor can be avoided. The measurement accuracy is increased, and filling levels of between just 0 and 200 ml or of between 0 and 300 ml can be measured in ml steps. This arrangement is suitable in particular for continuous measurement of the filling level and for determining the rate of filling.

This arrangement can also be combined with one or more inclination sensors, which are preferably likewise arranged on the suction pump housing. By using more than one filling level sensor, and with a suitable arrangement of said sensors, the inclination of the collection container can also be determined, such that no separate inclination sensors have to be used.

The elasticity of the coupling element can be obtained, on the one hand, by suitable choice of material and, on the other hand, by suitable shaping. A material is preferably used whose capacitive properties are equal to those of the fluid collection container.

The coupling element can be arranged on the fluid collection container. However, it is preferably arranged on the suction pump housing.

In both cases, the fluid collection container can be designed without sensors. In this way, it can be produced inexpensively and can be designed as a disposable product. It can therefore be discarded after its first use.

By virtue of the elasticity of the coupling element, the functionality of the sensor and of the measurement system is maintained even after the fluid collection container has been exchanged several times.

If the coupling element is arranged on the suction pump housing and thus covers the sensor face of the filling level sensor, this sensor face is protected from external influences, and the housing is easier to clean than if the sensor faces were exposed.

In a preferred embodiment, the filling level sensor is arranged in an outer side wall of the suction pump housing, and the coupling element protrudes from this side wall. It is pressed in elastically when the fluid collection container is secured on the housing and thus ensures an optimal and uniform dielectric transition from the sensor face of the filling level sensor to the outer wall of the container.

The coupling element can be secured on the filling level sensor, particularly on its sensitive surface, in particular by being welded thereon, melted thereon or integrally cast therewith. However, the filling level sensor is preferably embedded in the coupling element. In this way, the coupling element can at the same time serve as an assembly aid when securing the filling level sensor in the suction pump housing. In the case of the embedded filling level sensor, the coupling element can also serve at the same time or alternatively as a protective sheath for the filling level sensor.

In a preferred embodiment, this protective sheath has a base, the two opposite surfaces of which form the abovementioned first surface and the second surface. This base is surrounded by an at least partially encircling side wall that forms a hollow space, such that the filling level sensor can be arranged in this hollow space.

For securing in an opening of the suction pump housing, an at least partially encircling and outwardly protruding first flange is formed integrally on that end of the side wall opposite the base, and an outwardly protruding second flange is formed integrally on the base. These two flanges bear on both sides of the opening of the housing.

The filling level sensor is preferably arranged in the area below a vacuum attachment part of the suction pump housing leading to the suction pump. Alternatively or in addition, it can also be arranged obliquely at a distance from a secretion attachment part of the suction pump housing, which permits a connection to a patient-side secretion tube. In all these cases, contamination of the sensor by drops of fluid possibly emerging from the secretion attachment part is largely avoided.

BRIEF DESCRIPTION OF THE FIGURES

A preferred embodiment of the invention is described below with reference to the drawings, which serve only for explanatory purposes and are not to be interpreted as limiting the invention. In the drawings.

DETAILED DESCRIPTION

Figure 1:
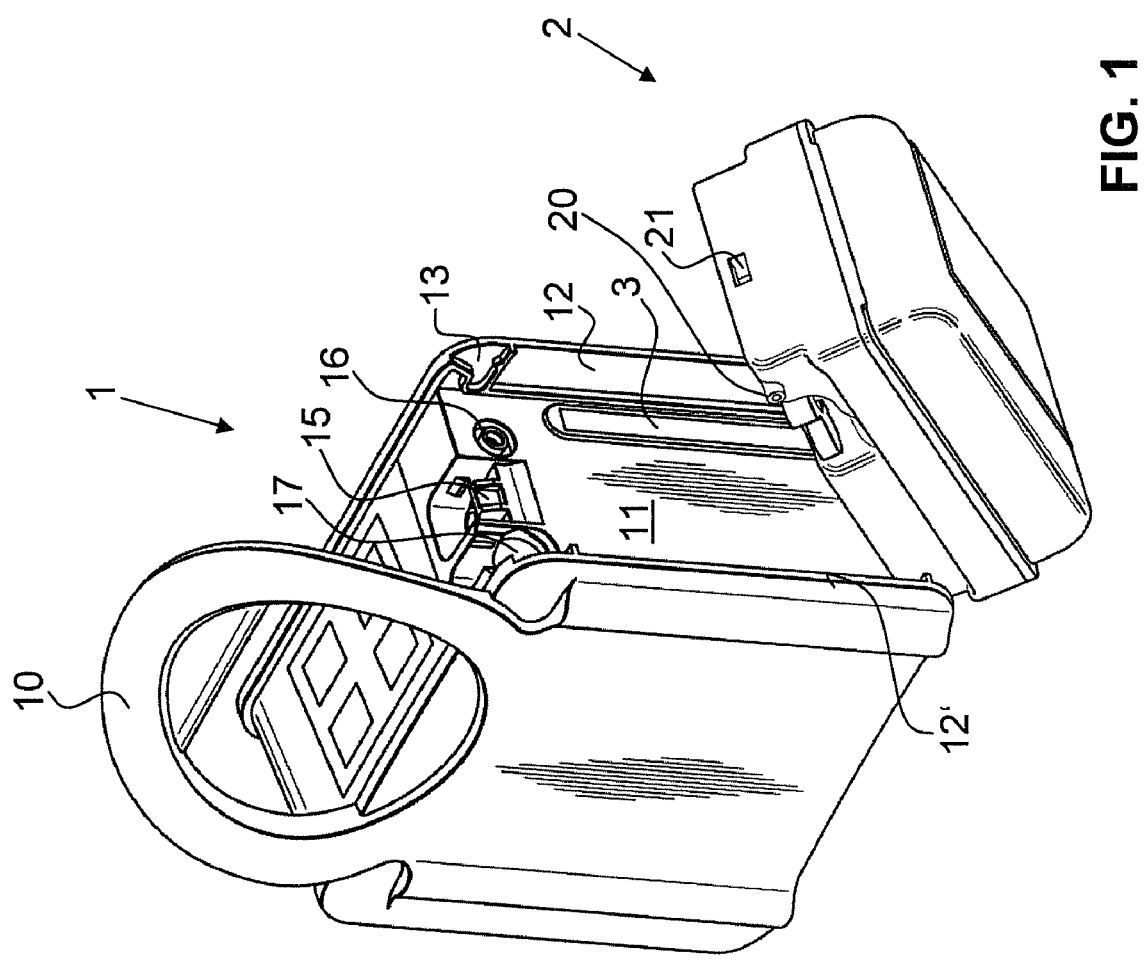
FIG. 1 shows a perspective view of a drainage pump unit with a fluid collection container according to the invention.
Figure 2:
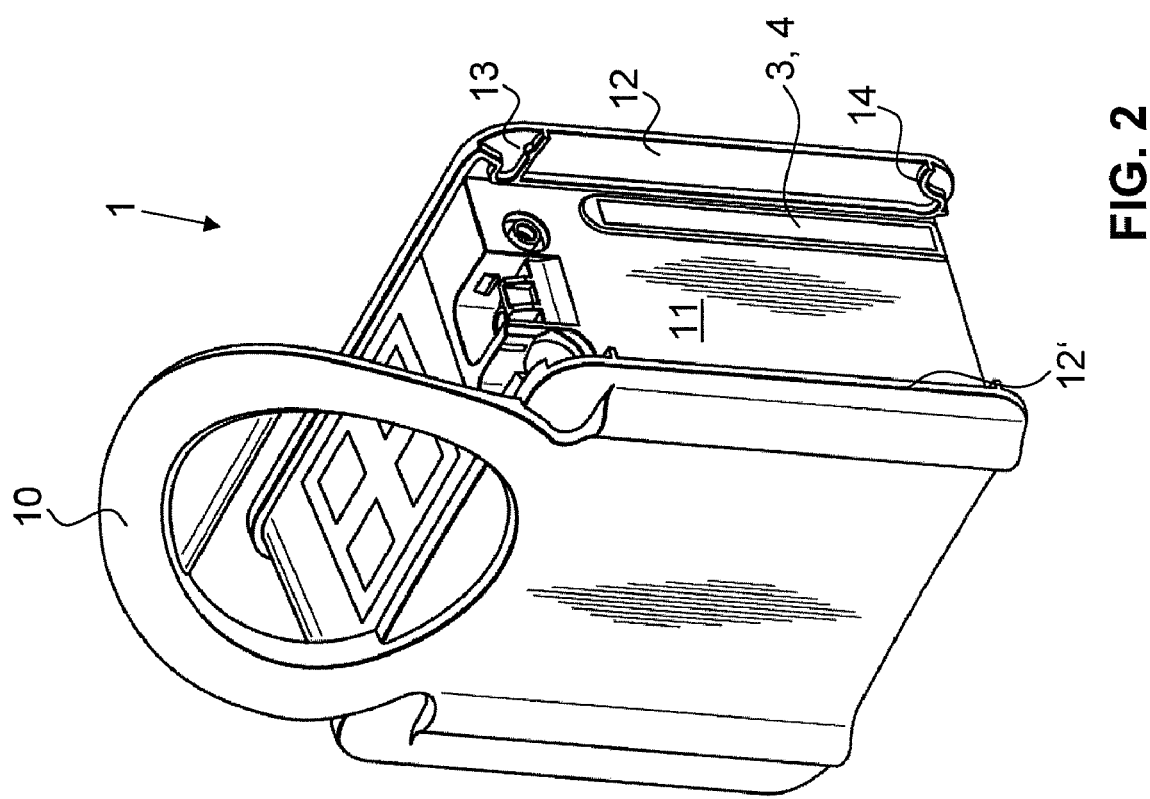
FIG. 2 shows the drainage pump unit according to FIG. 1 without the fluid collection container.

FIGS. 1 and 2 show a drainage pump unit, as is known in principle from, for example, WO 2007/128156 and WO 2008/141471. It has a suction pump housing 1 with a front wall 12, a back wall 12' and two side walls 11. The housing 1 can be portable, for example by means of a carrying handle 10. Alternatively or in addition to the carrying handle 10, the housing 1 preferably has a stand or feet, such that the housing, in the position depicted, can be placed on a table or on another suitable support surface. Comments made below regarding directions are to be interpreted in this standing position of the housing.

The housing 1 accommodates a concealed suction pump or vacuum pump and electronics for operating the pump and for evaluating measurement data from a service line possibly provided with sensors. The suction pump can be operated via a control panel arranged on the housing or control keys and/or buttons.

The suction pump housing 1 is cuboid in this example, with at least one outer side wall 11 of the housing being substantially planar. However, the suction pump housing 1 can also have another shape.

The front wall 12 and the back wall 12' protrude laterally from the planar side wall 11 of the housing and form, together with the side wall 11 of the housing, a recess for a fluid collection container 2.

This fluid collection container 2 is preferably substantially cuboid. The suction pump housing 1 and the fluid collection container 2 are preferably made of plastic.

The fluid collection container 2 is secured releasably on the suction pump housing 1. It is preferably swivelled in and locks in this position. For this purpose, the protruding part of the front wall 12 and of the back wall 12' have upper and lower slide guides 13, 14 in which upper and lower locking pins 20 of the fluid collection container 2 engage. Only an upper locking pin 20 can be seen in FIG. 1. The fluid collection container 2 has two mutually opposite upper and two mutually opposite lower locking pins 20, which all protrude from the same outer side wall of the container 2. With this side wall, the fluid collection container 2 bears on the side wall 11 of the suction pump housing 1. The side wall of the fluid collection container 2 is preferably likewise substantially planar.

The collection container 2 has a recess 21 in which a locking hook 15 arranged on the housing 1 latches and thus releasably fixes the collection container 2 in its position on the housing 1. Instead of slide guides, locking pins and locking hooks, the securing of the collection container 2 and its fixing can also be effected by other means.

A housing-side vacuum attachment part 16 is present in the side wall 11 of the housing 1. It is preferably arranged in an upper area of the side wall 11. In this example, the vacuum attachment part 16 is in the form of a connector piece which engages in a corresponding opening (not shown here) of the fluid collection container 2. The free end of the connector piece 16 is flush with the side wall 11 of the housing or is even set back relative to the latter in the direction of the housing 1. Thus, the connector piece 16 preferably does not protrude. To ensure that the vacuum connection formed by the connector piece 16 between housing 1 and container 2 is leaktight, the connector piece 16 of the housing 1 and/or the opening of the container 2 has a sealing ring (not shown here). To ensure that aspirated secretions collected in the container 2 cannot enter the housing 1, the vacuum attachment part 16 and/or the associated opening of the container 2 is preferably provided with one or more filters.

A housing-side secretion attachment part, or a recess 17 for attaching such an attachment part, is present in the upper area of the side wall 11, on the side opposite the vacuum attachment part 16. A pump-side attachment part of a patient-side drainage tube is able to be plugged in here, as is disclosed in WO 2008/141471. This secretion attachment part 17 is, like the vacuum attachment part 16, connected in a leaktight manner to a corresponding opening of the fluid collection container 2 when the fluid collection container 2 is secured on the housing 1, in this case swivelled into place. However, it is also possible for the connection between container 2 and patient-side drainage tube to be established in another way, for example by the tube also being able to be plugged in directly or via suitable coupling parts in the container 2.

By way of the vacuum attachment part 16, an underpressure is generated in the container 2 by means of the suction pump. By virtue of this underpressure, a fluid or secretion is aspirated from the cavity of the patient through the drainage tube and into the container 2 and collected there.

The device comprises at least one flat band-shaped capacitive filling level sensor 4. Filling level sensors of this kind are known from the prior art. They are planar and flat. Their length is substantially greater than their width and their thickness, and their width is also usually much greater than their thickness.

An evaluation unit (not shown here) is connected to the capacitive filling level sensor 4. This unit is preferably located in the housing 1. The capacitive filling level sensor 4 preferably permits a continuous measurement of the filling level and thus also permits the determination of a filling rate. However, it is also possible to measure at intervals or according to the requirements of the user.

The filling level sensor 4 is arranged in the side wall 11 of the housing 1, with its sensitive face preferably being directed towards the container 2. This sensitive face and therefore the sensor 4 extend in their longitudinal direction or longitudinal axis, preferably vertically from the bottom upwards. However, they can also be arranged obliquely. Moreover, more than one filling level sensor 4 can be present, in particular two or three filling level sensors 4. These can extend vertically at different locations and/or at different heights. However, one filling level sensor 4 can also extend vertically in its longitudinal direction and another filling level sensor can be arranged obliquely thereto. In this way, the inclination of the housing and of the container can also be determined when measuring the filling level, such that the measurement data relating to the filling level can be correspondingly corrected. However, other types of inclination sensors can also be used together with the filling level sensor.

An elastically configured coupling element 3 is present between sensor 4 and container 2. This coupling element 3 has a base 30 with two mutually opposite, planar parallel surfaces 300. In the secured state of the container 2, the sensor 4 preferably bears with its sensitive face on one of these surfaces. An outer wall of the container 2 bears on the second of these surfaces in this state. This second surface 300 preferably bears on the container 2 at least by a surface area corresponding to the surface area of the sensitive face. That is to say, it produces a connection of the whole sensitive face to the container wall.

The coupling element 3 is preferably made of silicone, PVC or rubber. Other materials with suitable dielectric properties can also be used, however. The coupling element preferably has similar capacitive properties to the material of the container 2.

In a simple embodiment, the sensor 4 is held in the housing 1 and its outwardly directed sensitive face is covered completely by this coupling element 3. However, the coupling element 3 preferably forms a sensor sheath, as can be seen clearly in FIGS. 3 to 7 and as is fitted into the housing 1 in FIGS. 1 and 2.

The sensor sheath 3 is preferably designed in one piece. Its length corresponds at least to the length of the sensor 4. It has the base 30 with the two planar parallel surfaces. A planar contact face 300 is present on the outer surface directed away from the housing 1 in the mounted state. The surface area of the contact face 300 corresponds at least to the surface area of the sensitive face, which sensitive face is covered completely by this contact face 300. This planar contact face 300 is preferably designed protruding slightly from the rest of the outer surface surrounding it. This can be seen clearly in FIG. 6.

A side wall 34 is integrally formed about at least part of the periphery of the inner side of the base 30 directed towards the housing 1 in the mounted state. The side wall 34 extends along the two long sides of the base 30 and one short side. The other short side is left open. The sensor sheath thus has an open end 31, and a closed end and also, in this case, a rounded end 32.

The free edge of this side wall 34 merges into an outwardly protruding first flange 35 which preferably has an inwardly protruding part 351. The side wall 34 is formed integrally on the base 30 and set back, such that it too forms an outwardly protruding second flange 33, which extends at a distance from but preferably parallel to the first flange 35. The second flange 33 is preferably of encircling design without any gaps. The first flange 35 can have gaps 350.

Figure 7:
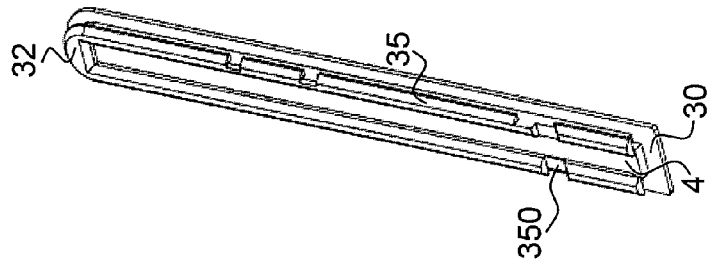
FIG. 7 shows a perspective view of the coupling element according to FIG. 3.
Figure 6:
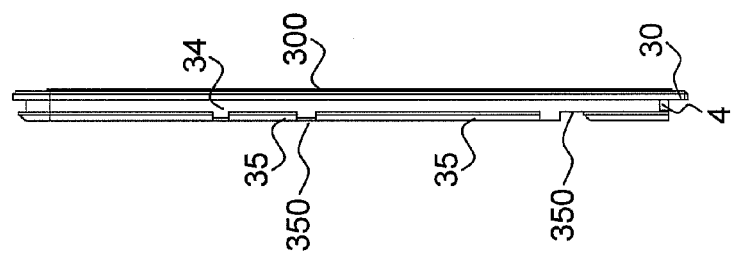
FIG. 6 shows the coupling element according to FIG. 3 in a second side view.
Figure 3:
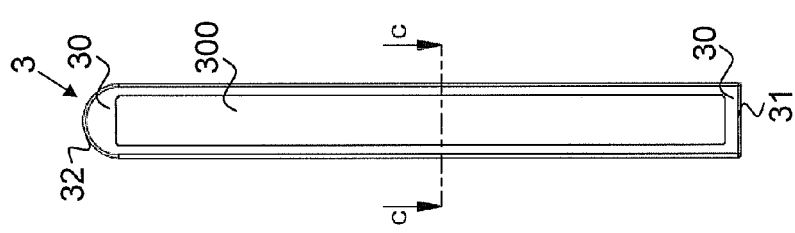
FIG. 3 shows a first side view of a coupling element according to the invention with a filling level sensor embedded therein.
Figure 4:
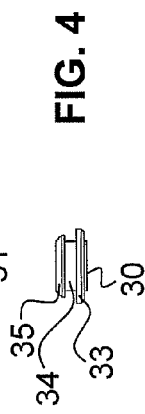
FIG. 4 shows the coupling element according to FIG. 3 in a view from below.
Figure 5:
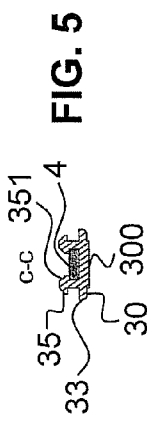
FIG. 5 shows a section through the coupling element according to FIG. 3 along C-C.

As can be seen in FIGS. 5, 6 and 7, the flat band-shaped capacitive sensor 4 can be pushed into this sensor sheath 3 and is held in the hollow space formed by the peripheral side wall 34 and the base 30. The inwardly protruding part 351 of the first flange 35 fixes the sensor 4 in its position. The sensitive face of the sensor 4 bears on the planar inner side of the base 30 and has its mating piece on the outer contact face 300, preferably parallel thereto, of the sensor sheath 3.

The sensor sheath 3 can now lock into the opening of the side wall 11 of the housing, with the first flange 35 coming to bear on the inside of the housing 1 and the second flange 33 bearing on the outside of the housing wall 11. The height of the side wall 34 of the sensor sheath therefore preferably corresponds approximately to the thickness of the side wall 11 of the housing.

When the fluid collection container 2 is now secured on the housing 1, the container 2 thus bears with its planar outer face on the whole contact face 300. The container 2 preferably deforms the contact face 300 and presses it in the direction of the housing 1, such that an optimal contact counter to a spring force is achieved. The whole arrangement is therefore preferably dimensioned such that the contact face 300 can be pressed in.

The drainage pump unit described here is only one illustrative embodiment of the implementation of the teaching according to the invention. For example, the pump housing and the drainage container can have another shape. Moreover, the vacuum and secretion attachment parts can have different designs and can be arranged at different locations. The coupling element can be designed differently, in particular not as a sensor sheath. Other modifications are possible.

By virtue of the elastically configured coupling element, the drainage pump unit according to the invention permits a filling level measurement even in the case of low filling amounts.

While the invention has been described herein with relation to certain embodiments and applications, those with skill in the art will recognize changes, modifications, alterations, and the like which still come within the spirit of the inventive concept, and such are intended to be within the scope of the invention as expressed in the following claims.

The invention claimed is:

1. A drainage pump unit for aspirating body fluids by means of a suction pump, the drainage pump unit comprising:
   a suction pump housing and a suction pump arranged in the suction pump housing;
   a fluid collection container being able to be secured releasably on the suction pump housing; and
   a flat band-shaped capacitive filling level sensor being arranged on the suction pump housing for the purpose of detecting a filling level in the fluid collection container wherein the drainage pump unit also comprises an elastically configured coupling element with a first surface and a second surface lying opposite the first surface, and the coupling element, in the secured state of the fluid collection container, bears with the first surface on the filling level sensor and with the second surface on an outer wall of the fluid collection container.

2. The drainage pump unit according to claim 1, in which the coupling element is arranged on the suction pump housing.

3. The drainage pump unit according to claim 2, in which the filling level sensor is arranged in an outer side wall of the suction pump housing, and the coupling element protrudes from the outer side wall.

4. The drainage pump unit according to claim 2, in which the filling level sensor is embedded in the coupling element.

5. The drainage pump unit according to claim 2, in which the coupling element has a base that forms the first surface and second surface, and in which the base is surrounded by an at least partially encircling side wall that forms a hollow space, and the filling level sensor is arranged in the hollow space.

6. The drainage pump unit according to claim 5, in which an at least partially encircling and outwardly protruding first flange is formed integrally on an end of the side wall of the coupling element opposite the base, and an outwardly protruding second flange is formed integrally on the base, the first and second flanges serving to secure the coupling element in an opening of an outer side wall of the suction pump housing.

7. The drainage pump unit according to claim 1, in which the first surface and second surface are planar and extend at least across an entire sensor face of the filling level sensor.

8. The drainage pump unit according to claim 1, in which the coupling element formed as one piece.

9. The drainage pump unit according to claim 1, in which the filling level sensor has a longitudinal axis and is arranged extending vertically on the suction pump housing along the longitudinal axis.

10. The drainage pump unit according to claim 1, in which the filling level sensor is arranged in an area below a vacuum attachment part of the suction pump housing leading to the suction pump.

11. The drainage pump unit according to claim 1, in which the filling level sensor is arranged obliquely at a distance from a secretion attachment part of the suction pump housing for connection to a patient-side secretion tube.

12. The drainage pump unit according to claim 1, in which the suction pump housing has an outer side wall, and in which the filling level sensor and at least one of a secretion attachment part and a vacuum attachment part, are arranged in the outer side wall.

13. The drainage pump unit according to claim 1, in which the coupling element is made of silicon, PVC or rubber.

14. The drainage pump unit according to claim 1, in which the coupling element is arranged on the fluid collection container.

15. A coupling element for use in a drainage pump unit comprising:
a base;
a first surface and a second surface lying opposite the first surface extending from the base; and
a filling level sensor located on the coupling element;
wherein the coupling element is made of an elastic material.

16. The coupling element of claim 15 wherein the coupling element is arranged on the suction pump housing.

17. The coupling element of claim 15 wherein the first surface and the second surface are planar and extend at least across an entire sensor face of the filling level sensor.

18. The coupling element of claim 15 wherein the coupling element is formed as one piece.

19. The coupling element of claim 15 wherein the filling level sensor is embedded in the coupling element.

20. The coupling element of claim 15 wherein the filling level sensor has a longitudinal axis and is arranged extending vertically on the drainage pump unit along the longitudinal axis.

* * * * *